United States Patent
Dalal et al.

(10) Patent No.: US 8,083,682 B2
(45) Date of Patent: Dec. 27, 2011

(54) SLEEP STATE DETECTION

(75) Inventors: Yousufali Dalal, St. Louis Park, MN (US); Yachuan Pu, Minneapolis, MN (US); John D. Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1474 days.

(21) Appl. No.: 11/458,602

(22) Filed: Jul. 19, 2006

(65) Prior Publication Data

US 2008/0033304 A1 Feb. 7, 2008

(51) Int. Cl.
*A61B 5/08* (2006.01)
*A61B 5/02* (2006.01)

(52) U.S. Cl. .................. 600/483; 600/484; 600/529

(58) Field of Classification Search .................. 600/483, 600/484, 529
See application file for complete search history.

(56) References Cited

U.S. PATENT DOCUMENTS

| 2005/0119711 A1* | 6/2005 | Cho et al. | 607/42 |
| 2007/0032733 A1* | 2/2007 | Burton | 600/509 |

OTHER PUBLICATIONS

Cysarz, D., et al., "A quantitative comparison of different methods to detect cardiorespiratory coordination during night-time sleep", *BioMedical Engineering Online*, 3:44, [online]. Retrieved from the Internet: <URL: http://www.biomedical-engineering-nline.com/content/pdf/1475-925X-3-44.pdf,(2004), 13 pgs.

Lee, D. S., et al., "Predicting Mortality Among Patients Hospitalized for Heart Failure", *JAMA*, 290(19), (2003), 2581-2587.

Legramante, J. M., et sl., "Sleep-related changes in baroreflex sensitivity and cardiovascular autonomic modulation", *Journal of Hypertension*, 21(8), (2003), 1555-1561.

Lotrič, M. B., et al., "Synchronization and modulation in the human cardiorespiratory system", *Physica A*, 283, (2000),451-461.

Pu, Y., "ECG-based screening tool for pediatric obstructive sleep apnea", *PhD Thesis—University of Minnesota*, (2005),179 pgs.

Schafer, C. , et al., "Heartbeat synchronized with ventilation", *Nature*, 392(6673), (Mar. 19, 1998), 239-240.

* cited by examiner

*Primary Examiner* — Patricia Mallari
*Assistant Examiner* — Christian Jang
(74) *Attorney, Agent, or Firm* — Schwegman, Lundberg & Woessner, P.A.

(57) ABSTRACT

This document discusses, among other things, systems and methods for determining sleep state, such as awake, sleeping, non-REM sleep, or REM sleep. Respiration and heart contractions are monitored. A cardio-respiratory ratio such as beats per breath is computed and used in the sleep state determination. Other information, such as heart rate variability (HRV), posture, and activity level can also be used in the sleep state determination. The sleep state information can be used to qualify or trigger storage of other physiological sensor data, or to permit remote sleep study monitoring of a subject, or to control or adjust one or more monitoring, diagnostic, or therapy algorithms, such as, for example a continuous positive airflow pressure (CPAP) device.

32 Claims, 6 Drawing Sheets

SLEEP STATE DETECTION

TECHNICAL FIELD

This patent document pertains generally to medical systems, devices, and methods, and more particularly, but not by way of limitation, to medical systems, devices, and methods for the detection of sleep state, such as sleep onset, using cardio-respiratory interactions.

BACKGROUND

Humans sleep to maintain health and well being. Certain sleep disorders may interfere with the ability to obtain a proper and healthy amount of sleep. Other diseases may also interfere with the ability to obtain sleep, or may be related to one or more types of sleep disorders. Similarly, certain sleep disorders may exist as co-morbidities with other health disorders. Furthermore, certain physiological variables may be affected by sleep or by circadian rhythms.

Sleep includes rapid eye movement (REM) sleep and non-REM (NREM or non-REM) sleep. Typically, sleep onset is NREM. Such NREM sleep can be conceptualized as including four stages, ranging from light to deep sleep. A NREM sleeping person typically cycles through these four stages of sleep approximately every 90 minutes. NREM sleep is typically followed by REM sleep, the most active stage of sleep when dreaming often occurs. During REM sleep, the eyes may move back and forth beneath the eyelids and muscles may become immobile.

Diagnosing sleep disorders, such as sleep apnea, typically involves conducting a sleep study in a hospital sleep laboratory. For example, congestive heart failure (CHF or HF) and other cardiac patients often exhibit sleep disorders as a co-morbidity. As a result, cardiologists routinely rely on hospital sleep laboratories to conduct testing on their patients. However, hospital sleep laboratory studies are expensive. Moreover, such studies require the patient to spend time at the sleep lab while the testing is conducted. In sum, sleep determination has many important and clinically useful applications.

OVERVIEW

This document discusses, among other things, systems and methods for determining sleep state, such as awake, sleeping, non-REM sleep, or REM sleep. Respiration and heart contractions are monitored. A cardio-respiratory ratio such as beats per breath is computed and used in the sleep state determination. Other information, such as heart rate variability (HRV), posture, and activity level can also be used in the sleep state determination. The sleep state information can be used to qualify or trigger storage of other physiological sensor data, or to permit remote sleep study monitoring of a subject, or to control or adjust one or more monitoring, diagnostic, or therapy algorithms, such as, for example a continuous positive airflow pressure (CPAP) device.

In Example 1, a system comprises an implantable heart contraction sensing circuit, a respiration sensing circuit, and a processor circuit, coupled to the heart contraction sensing circuit and the respiration sensing circuit, the processor circuit including a ratio module to compute a cardio-respiratory ratio of heart contractions to respiration cycles, and the processor circuit also including a variability module to compute a cardio-respiratory variability of the cardio-respiratory ratio.

In Example 2, the system of Example 1 can be optionally configured such that the processor includes a sleep state indicator determined using the cardio-respiratory variability.

In Example 3, the system of Examples 1-2 can be optionally configured such that the system includes or is coupled to a continuous positive airway pressure (CPAP) device, communicatively coupled to the processor to receive information about the sleep state indicator.

In Example 4, the system of Examples 1-3 can be optionally configured such that the system comprises a physiological sensor, the sensor providing a sensor output, wherein a status of the sleep state indicator is used to qualify the sensor output.

In Example 5, the system of Examples 1-4 can be optionally configured such that the sleep state indicator declares a sleeping state when the cardio-respiratory variability is less than a specified threshold value.

In Example 6, the system of Examples 1-5 can be optionally configured such that the sleep state indicator declares a sleeping state when a standard deviation of the cardio-respiratory variability is less than a specified threshold value.

In Example 7, the system of Examples 1-6 can be optionally configured such that the processor is communicatively couplable to a user interface to permit the threshold value to be changed by a user.

In Example 8, the system of Examples 1-7 can be optionally configured to include a time-variable threshold value to which the cardio-respiratory variability is compared.

In Example 9, the system of Examples 1-8 can be optionally configured such that the processor is communicatively couplable to a display device to display information derived from the cardio-respiratory ratio.

In Example 10, the system of Examples 1-9 can be optionally configured such that the display device displays a graph of the cardio-respiratory ratio.

In Example 11, the system of Examples 1-10 can be optionally configured such that the display of the graph of the cardio-respiratory ratio includes an indicator of sleep classification providing information about whether the sleeping state is REM or non-REM sleep.

In Example 12, the system of Examples 1-11 can optionally include a posture sensor circuit, to provide a posture information, and a sleep state indicator, coupled to the posture sensor circuit, the sleep state indicator determined using the cardio-respiratory variability and the posture information.

In Example 13, the system of Examples 1-12 can optionally include a heart rate variability circuit, to provide heart rate variability information, and a sleep state indicator, coupled to the heart rate variability circuit, the sleep state indicator determined using the cardio-respiratory variability and the heart rate variability.

In Example 14, the system of Examples 1-13 can optionally include an implantable device including at least the heart contraction sensing circuit and the respiration sensing circuit.

In Example 15, the system of Examples 1-14 can optionally include an implantable cardiac function management device including the processor.

In Example 16, the system of Examples 1-15 can optionally be configured such that the processor circuit includes a sleep state indicator determined using the cardio-respiratory variability, and in which the sleep state indicator is used to trigger storage or qualify information of at least one physiological sensor signal.

In Example 17, the system of Examples 1-16 can optionally be configured such that the sleep state indicator is used to trigger storage of at least one of a heart sound signal, a fluid accumulation status signal, or a blood pressure signal.

In Example 18, the system of Examples 1-17 can optionally be configured such that the processor circuit includes a sleep state indicator determined using the cardio-respiratory variability, and comprising an apnea indicator that uses information from the sleep state indicator.

In Example 19, the system of Examples 1-18 can optionally be configured such that the sleep state indicator is used to determine a time period over which an index of apnea or hypopnea events is computed.

In Example 20, a method includes detecting, using an implantable device, one or more heart contractions over a time period. At least one respiration is detected over the time period. A cardio-respiratory ratio of heart contractions to respiration cycles over the time period is determined. A cardio-respiratory variability of the cardio-respiratory ratio is determined.

In Example 21, the method of Example 20 can optionally include computing a sleep state indication using the cardio-respiratory variability.

In Example 22, the method of Examples 20-21 can optionally be configured such that computing a sleep state indication using the cardio-respiratory variability includes comparing the cardio-respiratory variability to a threshold value.

In Example 23, the method of Examples 20-22 can optionally be configured such that computing the sleep state indication using the cardio-respiratory variability includes comparing the cardio-respiratory variability to a time-variable threshold value.

In Example 24, the method of Examples 20-23 can optionally include communicating information about the sleep state indication to a continuous positive airway pressure (CPAP) device.

In Example 25, the method of Examples 20-24 can optionally include obtaining physiological sensor information, and qualifying the sensor information using the sleep state indication.

In Example 26, the method of Examples 20-25 can optionally include initiating or adjusting a response using the sleep state indication.

In Example 27, the method of Examples 20-26 can optionally include detecting a body position, and computing a sleep state indication using the body position and the cardio-respiratory variability.

In Example 28, the method of Examples 20-27 can optionally include detecting one or more body movements or postures, and computing a sleep state indication using the one or more body movements or postures and the cardio-respiratory variability.

In Example 29, the method of Examples 20-28 can optionally include detecting heart rate variability, and computing a sleep state indication using the heart variability and the cardio-respiratory variability.

In Example 30, a system comprises a means for implantably detecting one or more heart contractions over a time period, a means for detecting a respiration over the time period, a means for determining a cardio-respiratory ratio of heart contractions to respiration cycles over the time period, and a means for determining a cardio-respiratory variability of the cardio-respiratory ratio.

In Example 31, the system of Example 30 can optionally include a means for computing a sleep state indication using the cardio-respiratory variability.

In Example 32, the system of Examples 30-31 can optionally include a means for computing a sleep state indication using cardio-respiratory variability and heart rate variability.

In Example 33, a machine-readable medium provides instructions, which when carried out by one or more devices, cause the one or more devices to perform operations comprising receiving from an implantable device a signal associated with one or more heart contractions over a time period, receiving a signal associated with a respiration over the time period, determining a cardio-respiratory ratio of heart contractions to respiration cycles over the time period, and determining a cardio-respiratory variability of the cardio-respiratory ratio.

In Example 34, the machine readable medium optionally includes instructions for computing a sleep state indication using the variability.

This overview is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
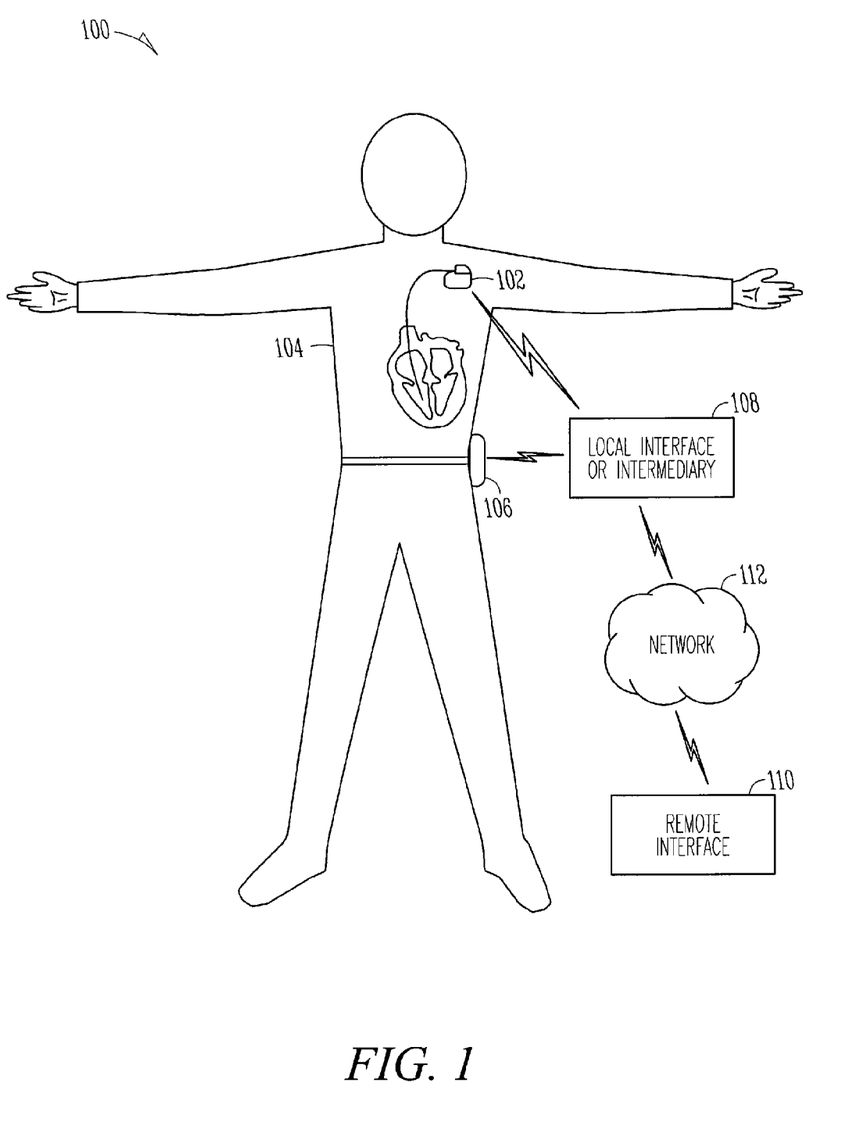
FIG. 1 is a schematic drawing illustrating generally an example of portions of a system that can be used to detect one or more sleep states, and portions of an environment in which it is used.

FIG. 1 is a schematic drawing illustrating generally an example of portions of a system 100 that can be used to detect one or more sleep states, and portions of an environment in which it is used. In certain examples, the system 100 includes an ambulatory personal medical device, such as an implantable medical device (IMD) 102 implanted in a subject 104 or an external physiological monitor 106, which can be worn by the subject 104. In certain examples, the IMD 102 includes a cardiac function management device, such as a pacer, cardioverter, defibrillator, cardiac resynchronization therapy (CRT) device, or an implantable drug delivery system or other implantable medical device for monitoring a patient or delivering a therapy to a patient, or as a separate implantable or external ancillary device to such implantable medical device. The IMD 102 or external physiological monitor 106 can be communicatively coupled to an external user interface or intermediary device, such as an external local programmer or other local interface or intermediary device 108. The IMD 102 or external physiological monitor 106 can also be communicatively coupled to a remote server or remote user interface 110, such as over a wired or wireless telecommunications or computer network 112. In certain examples, the system 100 uses a local intermediary 108 and remote server with a remote user interface 110, such as by using Guidant Corp.'s LATITUDE patient management system. The local user interface 108 or remote user interface 110 will generally include a display or other input or output mechanism.

Figure 2:
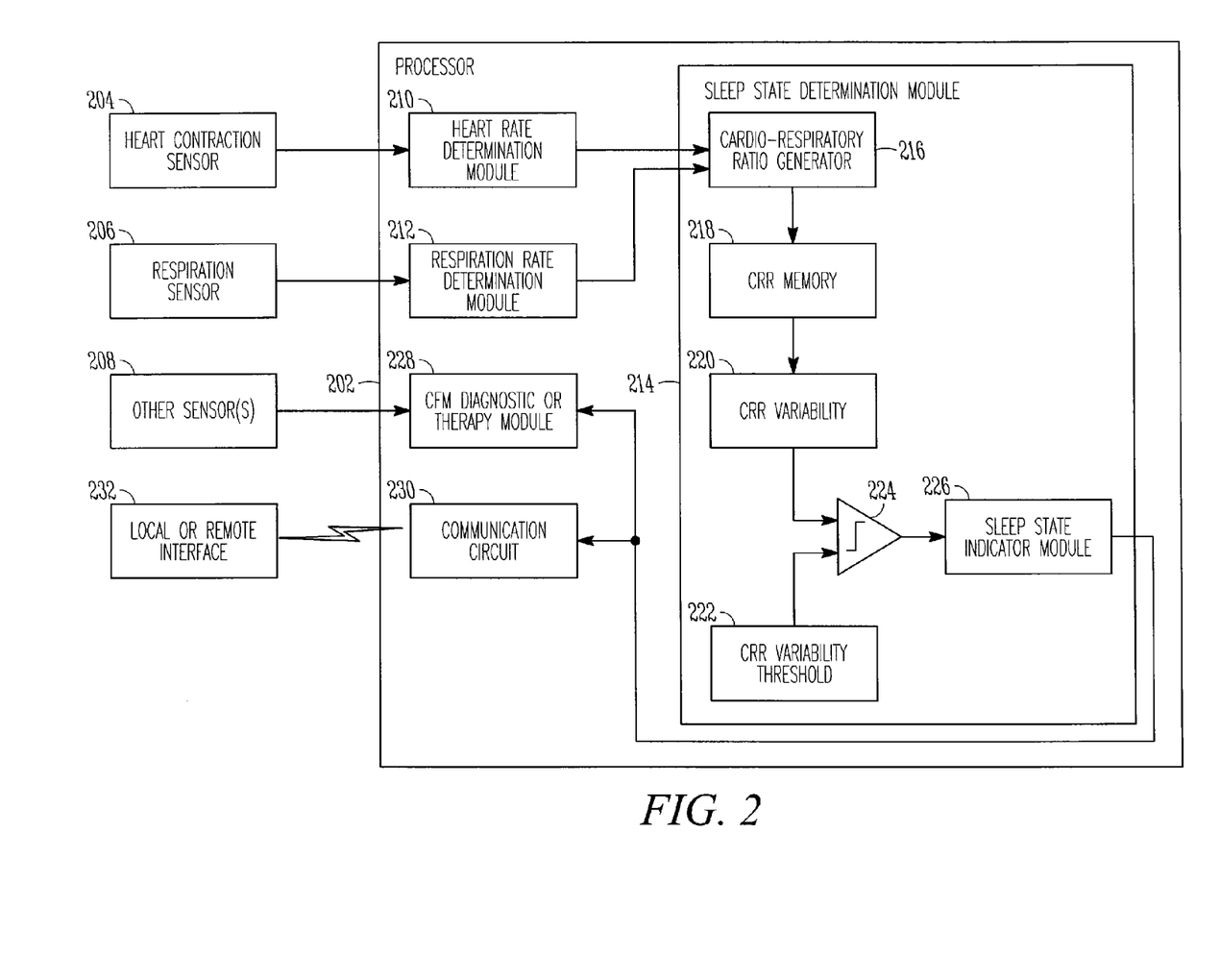
FIG. 2 is a schematic drawing illustrates generally an example of portions of the system.

FIG. 2 is a schematic drawing illustrates generally an example of portions of the system 100. In this example, the system 100 includes a processor 202 receiving inputs from a heart contraction sensor 204, a respiration sensor 206, or one or more other physiological sensors 208. The processor can include a microprocessor, controller, digital signal processor, or other processing components, and may be integrated into a single component or partitioned into more than one component.

In certain examples, the heart contraction sensor 204 includes an implantable intrinsic cardiac signal sensor to peak-detect, level-detect, or otherwise detect intrinsic depolarizations indicative of heart contractions, where such detection generally also involves frequency-selective filtering. In other examples, the heart contraction sensor 204 includes an implantable impedance sensor to detect heart contractions, such as via variations in a transthoracic or intracardiac impedance signal. In still other examples, the heart contraction sensor can detect information indicative of heart contractions from an acceleration signal, a sound signal, or a blood pressure signal. Information from multiple signals or sources can also be combined to detect heart contractions. In certain examples, the respiration sensor 206 includes an implantable transthoracic impedance sensor to peak-detect, level-detect, or otherwise detect impedance variations resulting from breathing, where such detection generally also involves frequency-selective filtering. In various other examples, respiration information can be obtained from other signals or sources, such as from a blood pressure signal, a sound signal, or any other suitable sensor. The system 100 can additionally or alternatively include implantable or external other sensors 208, such as an acceleration sensor to detect patient activity, a position sensor to detect patient posture, a heart sound sensor to detect patient heart sounds, a weight sensor to sense patient weight, or any other suitable sensor for detecting one or more physiologic signals.

In the example of FIG. 2, the processor 202 includes a heart rate determination module 210, which is coupled to the heart contraction sensor, and which detects the time interval between successive heart contractions, or heart rate. In this example, the processor 202 also includes a respiration rate determination module 212, which detects the time interval between successive breaths, or breathing rate. A sleep state determination module 214 receives the heart rate and breathing rate information from the heart rate determination module 210 and the respiration rate determination module 212, respectively. In certain examples, the sleep state determination module 212 includes a cardio-respiratory ratio (CRR) generator 216, which computes a CRR, such as by dividing a number of heart contractions by the number of respiration cycles occurring during a particular time period of interest, such as shown in the example of Equation 1.

$$CRR = (\text{Heart Contractions}) \div (\text{Respiration Cycles}) \quad (1)$$

The CRR generator 216 can compute the CRR recurrently, such as periodically, for example, over a specified fixed-length time window preceding such CRR computation. A CRR memory 218 receives and stores the computed CRR values, such as recent CRR values stored in a first-in-first-out (FIFO) or other buffer. A CRR variability module 220 can receive some or call of these stored CRR values for computing a CRR variability indicator, such as a variance, standard deviation, minimum-maximum spread difference, interquartile range, or the like. As an illustrative example, the CRR values stored in the buffer can be used to form a histogram, and an interquartile range or other characteristic of the spread of the histogram data can be used as a CRR variability indicator.

In the example of FIG. 2, the processor 202 includes a memory location having at least one stored CRR variability threshold value 222. In certain examples, a comparator 224 compares the CRR variability indicator to the CRR variability threshold value 222. The result of the comparison is provided to a sleep state indicator module 226, where it is used to provide an indication of sleep state, such as whether the patient is sleeping or awake or, if sleeping, whether the patient is in REM sleep or NREM sleep. In an illustrative example, if the CRR variability drops below a specified threshold value, the patient is deemed to be in NREM sleep. In other examples, the sleep state determination is made using information about the patient's previous sleep state, as discussed further below. In certain examples, the sleep state indicator is provided to a cardiac function management diagnostic or therapy control module 228. In certain examples, the cardiac function management diagnostic or therapy control module 228 also receives information from one or more other physiologic sensors 208, and the sleep state indicator can be used for, among other things, qualifying the information received from the one or more other physiologic sensors 208.

Additionally or alternatively, the sleep state indicator can be provided to a communication circuit 230, such as for communication to an external local or remote interface 232 for display, trending, or further processing. The example of FIG. 2 is particularly useful where the heart contraction sensor 204, the respiration sensor 206, and the processor 202 are embodied in an implantable cardiac function management device, since other monitoring or therapy functions can benefit from knowing whether the patient is sleeping or awake, or whether the patient is in REM or NREM sleep.

Figure 3:
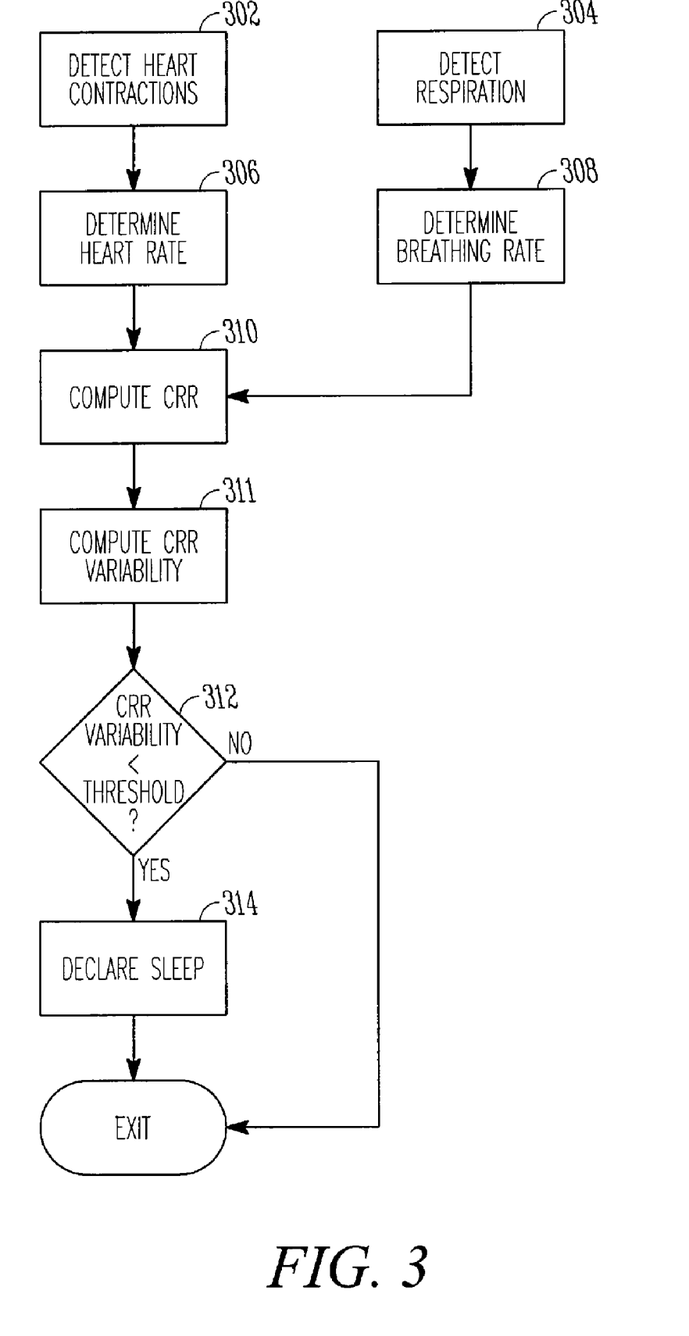
FIG. 3 is a flow chart illustrating generally an example of a method of detecting sleep state, such as by using the system of FIG. 2.

FIG. 3 is a flow chart illustrating generally an example of a method of detecting sleep state, such as by using the system 200 of FIG. 2. At 302, heart contractions are detected. Concurrently, at 304, respiration is detected. At 306 heart rate is determined, such as from the time interval between successive ventricular contractions. Concurrently, at 308, breathing rate is detected, such as from the time interval between successive breaths. Cardiorespiratory interaction can be conceptualized as a number of heart beats in each breath. A CRR can be computed at 310 by dividing, over a particular time period of interest, a number of heart contractions by the number of breaths occurring during the same time period. At 311, a CRR variability, such as a standard deviation, variance, minimum-maximum difference spread, or the like is computed. It may be desirable, before performing the variability computation, to exclude any CRR outliers from the computation, such as by establishing a band of reasonable CRR values, and excluding from consideration any values that fall outside the band deemed reasonable. At 312, the CRR variability is compared to a CRR variability threshold value. When the CRR variability falls below the CRR variability threshold, onset of sleep is declared at 314. In certain examples, a CRR variability threshold of 1 beat per breath that continues over a specified time period is used. In other examples, the CRR variability threshold is set between 1 beat per breath and 2 beats per breath. In certain examples, there is also a time requirement on the comparison, such that the CRR variability must fall below the CRR variability threshold for a specified time period (e.g., 30 seconds) in order for onset of sleep to be declared at 314. In other examples, the comparison can include hysteresis, such as by providing multiple threshold values that are relatively close in value, such as to prevent bouncing between sleeping and awake states.

Figure 4:
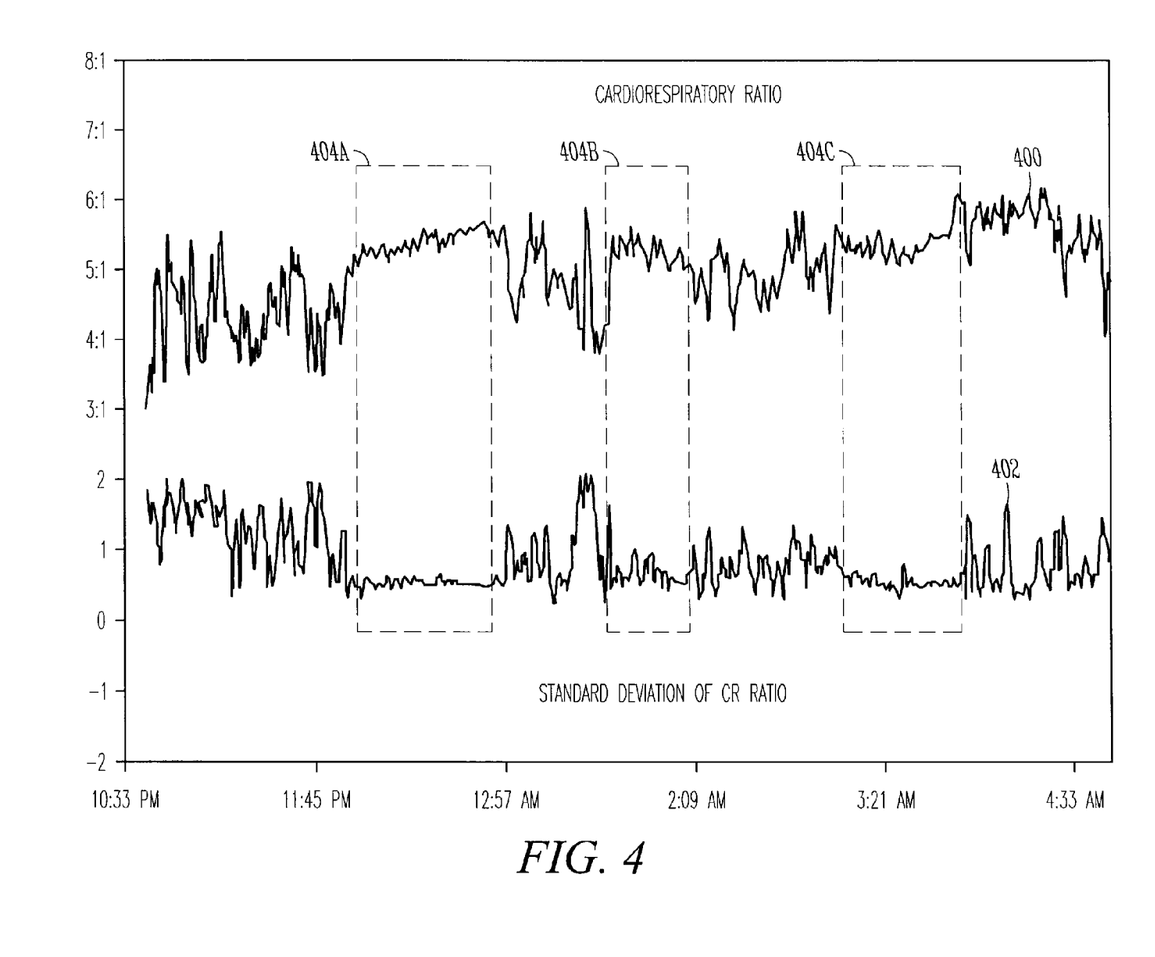
FIG. 4 is a graph of an example of CRR and its standard deviation over a time period taken at night.

FIG. 4 is a graph of an example of CRR and its standard deviation over a time period taken at night. In the example of FIG. 4, the CRR signal 400 and CRR standard deviation signal 402 are marked with regions 404A, 404B, and 404C denoting NREM sleep periods for which the standard deviation of CRR fell below a threshold value of 1 beat per breath for at least 30 seconds. In this example, the CRR was computed over a moving window time interval corresponding to 5 breaths, and the CRR standard deviation was obtained using 2-3 successive CRR values separated from each other in time by 30 seconds. In certain examples, information such as shown in the graph of FIG. 4 is displayed on for a user, such as on external local interface 108 or external remote interface 110.

In general, NREM sleep is associated with low CRR variability, such as less than the CRR variability threshold of 1 beat per breath for a specified time period, as discussed above. High CRR variability can be associated with either REM sleep, arousal from sleep, sleep disordered breathing, or being awake. Therefore, it may be desirable, for example, to use another indicator to also distinguish REM sleep from being awake.

Figure 5:
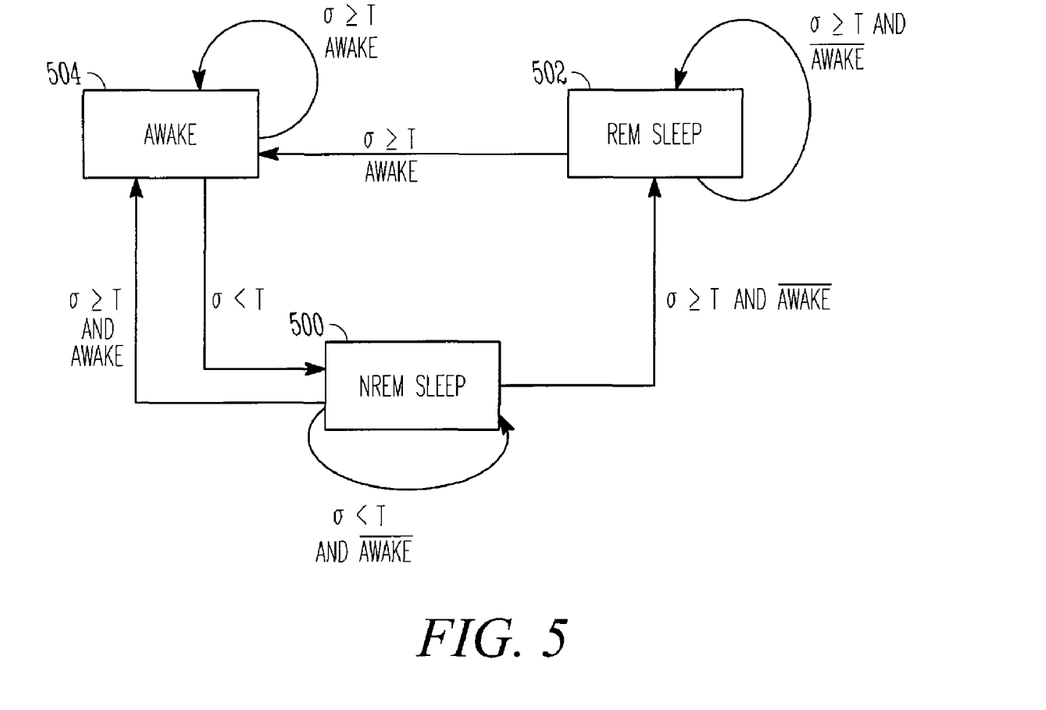
FIG. 5 is a state diagram illustrating an example of providing three distinct states: NREM sleep, REM sleep, and awake.

FIG. 5 is a state diagram illustrating an example of providing three distinct states: NREM sleep 500, REM sleep 502, and awake 504. As shown in FIG. 5, a person will not enter the REM sleep state 502 directly from the awake state 504; instead, the person enters the REM sleep state 502 only through the NREM sleep state 500. The state diagram of FIG. 5 lists the relationship between CRR variability (denoted, in this example, by its standard deviation σ) and the CRR variability threshold value (denoted by T), and at least one other proxy indicator of being awake (denoted as "AWAKE"). Using this other indicator, AWAKE, as shown in FIG. 5, it is possible to distinguish between awake, NREM sleep, and REM sleep states.

For instance, in an example in which the other sensors 208 includes an accelerometer, a tilt switch, or other posture detector, if the CRR variability exceeds the CRR variability threshold and the patient is not supine, the patient can be declared awake. If the CRR variability exceeds the CRR variability threshold but the patient is supine, the patient can be declared in REM sleep. If the CRR variability falls below the CRR variability threshold, the patient can be declared in NREM sleep. If the CRR variability falls below the CRR variability threshold and the patient is not supine, the patient can be declared to be in an indeterminate state.

Other sensors can be additionally or alternatively used, such as to improve the sleep determination. For instance, in an example in which the other sensors include an activity sensor, such as an accelerometer that information can be used. It can be assumed that REM sleep, which may involve some activity, does not involve as much activity as being awake. Therefore, the patient's activity level can be compared to an activity level threshold to distinguish between REM sleep and being awake—either in addition to, or as an alternative to the posture sensor. For example, if the CRR variability exceeds the CRR variability threshold and the activity level exceeds the awake activity level threshold, then the patient can be declared awake. If the CRR variability exceeds the CRR variability threshold and the activity level is less than the awake activity level threshold, then the patient can be declared in REM sleep. If the CRR variability falls below the CRR variability threshold, then the patient can be declared in NREM sleep. If the CRR variability threshold falls below the CRR variability threshold and the activity level exceeds the awake activity level threshold, then the patient can be declared in an indeterminate state—or the posture sensor can be used to resolve the indeterminate state if the patient is supine, in which case the patient can be declared in NREM sleep.

Similarly, one or more other indicators can also be used to generate a sleep state, because other physiological indicators are affected by sleep state. For example, the balance between the patient's sympathetic and parasympathetic nervous systems (sometimes referred to as autonomic tone or autonomic balance) is affected by sleep state. In general, parasympathetic activity normally increases during NREM sleep. During REM sleep, and particularly during phasic REM sleep, sympathetic activity typically increases to balance out the NREM sleep increase in parasympathetic activity. Heart rate variability (HRV) is an indicator of autonomic balance, with more heart rate variability generally indicative of a good balance between sympathetic and parasympathetic activity. An LF/HF ratio of a low frequency component of HRV to a higher frequency component of HRV can be used as a proxy for a sympathetic/parasympathetic activity ratio. Therefore, an NREM sleep determination can be made by comparing HRV to a corresponding HRV threshold value, or by comparing the LF/HF ratio of HRV to a corresponding LF/HF threshold value. The HRV-based NREM sleep determination can be used to qualify the CRR-based NREM sleep determination, or vice-versa. In general, CRR variability can be used in conjunction with other measured physiological indicators, such as HRV, posture, activity, or the like, and a set of rules, fuzzy logic, a neural network, or the like can be applied to distinguish between NREM sleep, REM sleep, and awake states.

In certain examples, a rapid eye movement (REM) sensor can be used to distinguish between REM and NREM sleep states, if available. In certain examples, a limb muscle tone sensor can be used to distinguish between REM and awake states, since an awake state typically demonstrates more limb muscle tone than an asleep state.

Figure 6:
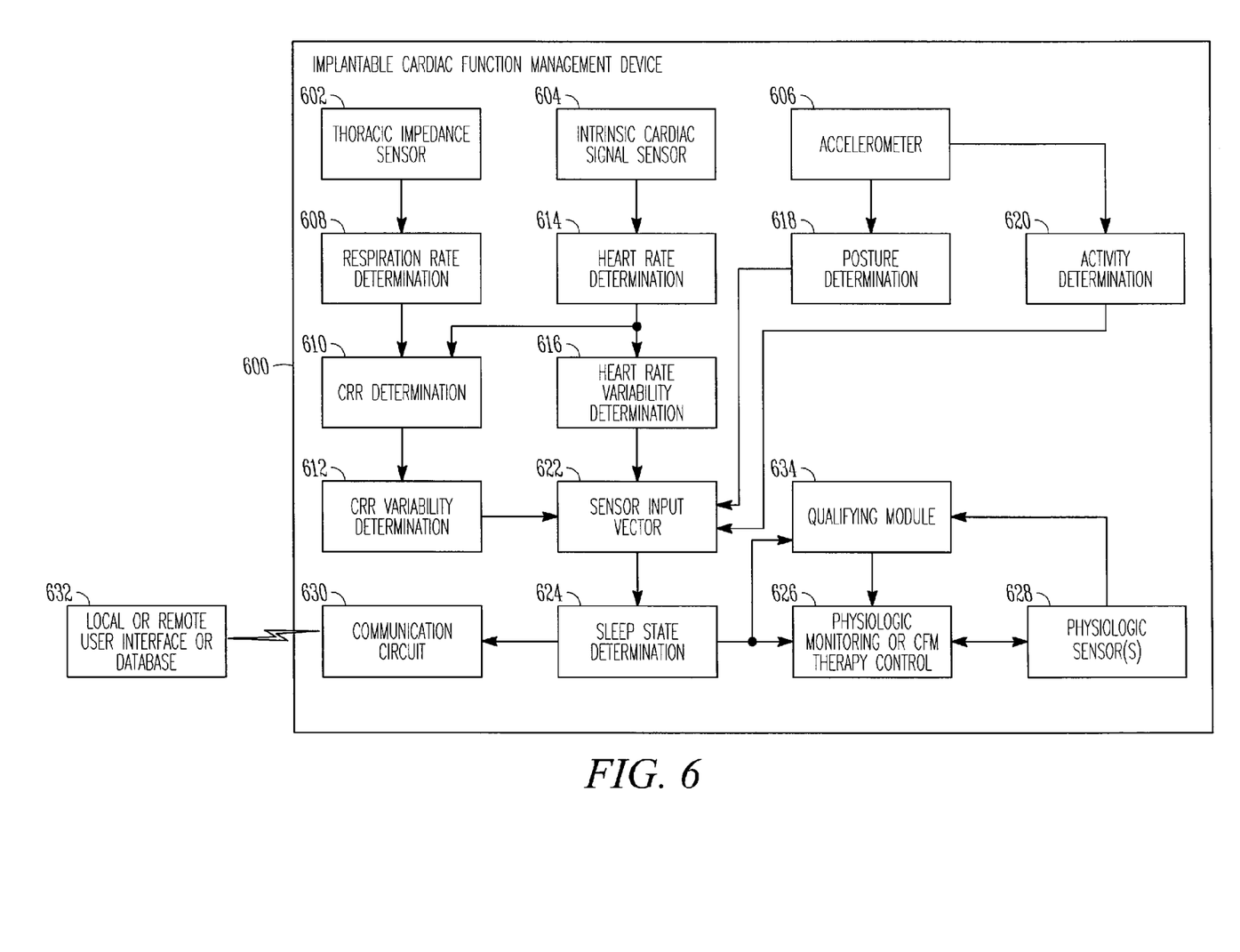
FIG. 6 illustrates an example of an implantable medical device, such as an implantable cardiac function management (CFM) device for performing a sleep state determination.

For example, FIG. 6 illustrates an example of an implantable medical device, such as an implantable cardiac function management (CFM) device 600 for performing a sleep state determination, such as by using CRR variability and other physiological sensor information to distinguish between NREM sleep, REM sleep, and awake states, for example. In the example of FIG. 6, the implantable CFM device 600 can include a thoracic impedance sensor 602 or other respiration sensor, an intrinsic cardiac signal sensor 604 or other heart contraction sensor, and an accelerometer 606 or other posture or activity sensor.

Information received from the thoracic impedance sensor 602 can be used by a respiration rate determination module 608, such as to determine respiration rate. The respiration rate information, in turn, can be used by a CRR determination module 610, such as to determine a CRR value. The CRR values, in turn, can be used by a CRR variability determination module 612, such as to determine an indication of CRR variability, such as for use in comparing to a CRR variability threshold value as a sleep indicator.

Information received from the intrinsic cardiac signal sensor 604 can be used by a heart rate determination module 614, such as to determine a heart rate. The heart rate information, in turn, can be provided to the CRR determination module 610, such as for its CRR determination. The heart rate information can also be provided to a heart rate variability (HRV) determination module 616, such as to compute an indication of heart rate variability.

Information received from the accelerometer 606 can be used by a posture determination module 618, such as to determine the subject's posture, for example, whether the patient is supine, upright, or reclining. Information received from the accelerometer 606 can also be used by the activity determination module 620, such as to determine an activity level of the patient.

The CRR variability information, the heart rate variability information, the posture information, and the activity level information can be aggregated into a multivariate sensor input vector 622. The sensor input vector 622 is provided to the sleep state determination module 624, such as to determine the patient's sleep state, for example, whether the patient is awake, in NREM sleep, or in REM sleep, such as described above with respect to FIG. 5. One or more values of the resulting sleep state determination can be stored in a memory device in or coupled to the sleep state determination module 624 or can be communicated to a physiologic monitoring or CRM therapy control module 626, where information about the patient's sleep state can be used in numerous ways.

For example, this information can be used to schedule readings from one or more other physiologic sensors 628 (or even from the impedance sensor 602, the intrinsic cardiac signal sensor 604, or the accelerometer 606). For example, it may be desirable to obtain such physiological information only when the subject is in a particular sleep state, or is in certain particular sleep states. For example, it may be desirable to only obtain heart sound information from an acoustic sensor during sleep, or only during NREM sleep. Sleep state information can be used to appropriately trigger or schedule such readings, or to qualify one or more readings that occur regardless of sleep state, such as by using a qualifying module 634. As another example, sleep provides a time window for better assessing autonomic nervous system (ANS) activity, and the stationarity of sleep may reflect a patient's baseline physiology or pathophysiology, thus providing useful diagnostic information.

In another example, it may be desirable to collect physiological information in more than one sleep state, but to segregate information received from one or more such physiological sensors according to the particular sleep state in which it was acquired. In yet another example, the sleep state information can be used to adjust one or more physiological signal processing parameters or one or more monitoring or therapy parameters. In certain examples, information about the sleep state or information from the sensor input vector 622 is provided by the sleep state determination module 624 to a communication circuit 630, such as for being wirelessly or otherwise communicated from the implantable cardiac function management device 600 to an external local or remote user interface or database 632. The sleep state can be displayed on a monitor of such local or remote user interface, such as in conjunction with other physiological information. In certain examples, this helps a physician better understand the sleep state and other physiological information, such as for making a diagnosis or adjusting patient therapy. The external remote or local user interface 632 can also be used to permit a physician or other caregiver to adjust one or more parameters associated with the sleep state determination, such as by allowing a particular value of the CRR variability threshold value to be programmed by the user, by allowing the user to specify whether posture, activity level, or the like should be considered and used in the sleep state determination, or the like.

In another example, the CRR variability threshold value could be automatically adaptively adjusted. In one such an automatic adaptive example, once sleep onset is detected (e.g., based on the CRR variability falling below an absolute CRR variability threshold value for a specified period of time), a new CRR variability threshold value is established, such as by setting the CRR variability threshold value at a specified increment above the lowest detected (or other specified detected) CRR variability value. The amount of the specified increment can be fixed, or it can be a function of the detected CRR variability. Additionally or alternatively, the CRR variability threshold value can also be made a function of time. For example, the CRR variability threshold value can be initially set at the absolute CRR variability threshold value for detecting sleep onset, but can then decay slowly (e.g., exponentially) toward the lowest detected CRR variability value for declaring an awake state. This example would be more sensitive to transitions from sleep to awake. Conversely, it may be desirable to make the system less sensitive to a sleep state transition (e.g., it may be desirable to add time-sensitive hysteresis). As an example, the CRR variability threshold can be initially set to the lowest detected CRR variability value plus the specified increment, as discussed above, but can then increase slowly (e.g., as function $1-e^{-t/\tau}$) toward the absolute CRR variability threshold value. Such examples can be conceptualized as providing a type of "automatic gain control" (AGC) on the CRR variability threshold value.

In general, cardiologists, including physicians treating heart failure patients, must often rely on hospital sleep laboratories to conduct further testing on their patients. However, with the above-described capabilities already incorporated in an implantable cardiac function management device 600 in such patients, such doctors will be able to obtain sleep study information (e.g., stored intrinsic cardiac signal, stored respiration signal, stored activity level signal, stored heart rate variability signal, sleep state signal, or the like) by simply uploading such information from the implantable device 600 to the external local or remote user interface or database 632, where such information can be displayed. Having such sleep state information readily available or even displayable with such other physiological information (e.g., respiration, HRV, etc.) will make it much easier for a physician to diagnose respiration disorders, such as sleep disordered breathing, apnea, or the like. Moreover, if the patient is using a Continuous Positive Airflow Pressure (CPAP) or other like ancillary device having a communication interface, such information can also be communicated to the remote or local user interface or database 632, such that a physician can evaluate the effectiveness of the CPAP therapy or other ancillary therapy on the patient's cardio-respiratory status. Moreover, for a remote user interface, the patient need not even appear for a doctor's appointment, since sleep study information can be remotely uploaded. Furthermore, with the sleep state information provided as discussed above, the implantable cardiac function management device 600 can be programmed to automatically offer different therapies (e.g., pacing mode, cardiac resynchronization therapy mode) for a sleeping patient than for an awake patient.

In certain examples, the above-described sleep state indicator can be used in determining or providing an indicator of apnea events. For example, an apnea or hypopnea detector may include a respiration sensor to determine apnea events (e.g., an episode of cessation of breathing for at least 10 seconds) or hypopnea events (e.g., an episode of shallow breathing for at least 10 seconds). The sleep state indicator may be used to qualify such an indication of apnea or hypopnea, such that such events are only counted when the sleep state indicator indicates that the subject is sleeping. Additionally or alternatively, the sleep state indicator can be used to determine a time period over which an apnea-hypopnea index (AHI) is computed, where the AHI is the number of apnea or hypopnea events occurring during the time period that the sleep state indicator indicates is spent sleeping.

The above description has particularly emphasized an example in which hospital sleep lab information can be obtained using an implantable cardiac function management device. However, certain aspects of the above systems and methods may also be useful outside of this context. For example, instead of using an implantable cardiac function management device (such as a pacer, defibrillator, or the like) to sense heart contractions or breathing, such information could alternatively be obtained using an external device. In one such example, the external device could be worn like a wristwatch, and can sense heart contraction information and breathing information from a commercially available blood pressure sensor. In certain examples, such an external device can be used to communicate with an implantable device, or with another external device, such as an external CPAP machine, for example, to monitor efficacy of the CPAP therapy, or even for closed-loop adjustment of one or more CPAP parameters.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A system comprising:
    an implantable heart contraction sensing circuit;
    a respiration sensing circuit;
    a processor circuit, coupled to the heart contraction sensing circuit and the respiration sensing circuit, the processor circuit including a ratio module to compute a cardio-respiratory ratio of heart contractions to respiration cycles, and the processor circuit also including a variability module to compute a cardio-respiratory variability of the cardio-respiratory ratio, wherein the processor circuit includes a sleep state indicator including a sleep state indicator value determined using the cardio-respiratory variability, wherein the sleep state indicator declares a sleeping state when the cardio-respiratory variability is less than a specified threshold value.

2. The system of claim 1, in which the processor circuit includes a sleep state indicator determined using the cardio-respiratory variability and at least one other physiological indicator.

3. The system of claim 1, comprising a continuous positive airway pressure (CPAP) device, communicatively coupled to the processor to receive information about the sleep state indicator.

4. The system of claim 1, comprising a physiological sensor, the sensor providing a sensor output, wherein a status of the sleep state indicator is used to qualify the sensor output.

5. The system of claim 1, wherein the sleep state indicator declares a sleeping state when a standard deviation of the cardio-respiratory variability is less than a specified threshold value.

6. The system of claim 1, in which the processor is communicatively couplable to a user interface to permit the threshold value to be changed by a user.

7. The system of claim 1, comprising a time-variable threshold value to which the cardio-respiratory variability is compared.

8. The system of claim 1, in which the processor is communicatively couplable to a display device to display information derived from the cardio-respiratory ratio.

9. The system of claim 8, wherein the display device displays a graph of the cardio-respiratory ratio.

10. The system of claim 9, wherein the display of the graph of the cardio-respiratory ratio includes an indicator of sleep classification providing information about whether the sleeping state is REM or non-REM sleep.

11. The system of claim 1, comprising:
    a posture sensor circuit, to provide a posture information; and
    a sleep state indicator, coupled to the posture sensor circuit, the sleep state indicator including a sleep state indicator value determined using the cardio-respiratory variability and the posture information.

12. The system of claim 1, comprising:
    a heart rate variability circuit, to provide heart rate variability information; and a sleep state indicator, coupled to the heart rate variability circuit, the sleep state indicator including a sleep state indicator value determined using the cardio-respiratory variability and the heart rate variability.

13. The system of claim 1, comprising an implantable device including at least the heart contraction sensing circuit and the respiration sensing circuit.

14. The system of claim 13, comprising an implantable cardiac function management device including the processor.

15. The system of claim 1, in which the processor circuit includes a sleep state indicator including a sleep state indicator value determined using the cardio-respiratory variability, and in which the sleep state indicator is used to trigger storage or qualify information of at least one physiological sensor signal.

16. The system of claim 15, in which the sleep state indicator is used to trigger storage of at least one of a heart sound signal, a fluid accumulation status signal, or a blood pressure signal.

17. The system of claim 1, in which the processor circuit includes a sleep state indicator determined using the cardio-respiratory variability, and comprising an apnea indicator that uses information from the sleep state indicator.

18. The system of claim 17, in which the sleep state indicator is used to determine a time period over which an index of apnea or hypopnea events is computed.

19. A machine-assisted method comprising:
detecting, using an implantable device, one or more heart contractions over a time period;
detecting at least one respiration over the time period;
determining a cardio-respiratory ratio of heart contractions to respiration cycles over the time period;
determining a cardio-respiratory variability of the cardio-respiratory ratio; and
computing a sleep state indication using the cardio-respiratory variability, wherein computing a sleep state indication using the cardio-respiratory variability includes comparing the cardio-respiratory variability to a threshold value.

20. The method of claim 19, comprising computing a sleep state indication using the cardio-respiratory variability and at least one other physiological indicator.

21. The method of claim 19, wherein computing the sleep state indication using the cardio-respiratory variability includes comparing the cardio-respiratory variability to a time-variable threshold value.

22. The method of claim 19, comprising communicating information about the sleep state indication to a continuous positive airway pressure (CPAP) device.

23. The method of claim 19, comprising:
obtaining physiological sensor information;
qualifying the sensor information using the sleep state indication.

24. The method of claim 19, comprising initiating or adjusting a response using the sleep state indication.

25. The method of claim 19, comprising:
detecting a body position; and
computing a sleep state indication using the body position and the cardio-respiratory variability.

26. The method of claim 19, comprising:
detecting one or more body movements or postures; and
computing a sleep state indication using the one or more body movements or postures and the cardio-respiratory variability.

27. The method of claim 19, comprising
detecting heart rate variability; and
computing a sleep state indication using the heart variability and the cardio-respiratory variability.

28. A system comprising:
a means for implantably detecting one or more heart contractions over a time period;
a means for detecting a respiration over the time period;
a means for determining a cardio-respiratory ratio of heart contractions to respiration cycles over the time period;
a means for determining a cardio-respiratory variability of the cardio-respiratory ratio; and
a means for computing a sleep state indication using the cardio-respiratory variability, wherein the means for computing a sleep state indication declares a sleeping state when the cardio-respiratory variability is less than a specified threshold value.

29. The system of claim 28, comprising a means for computing a sleep state indication using the cardio-respiratory variability and at least one other physiological indicator.

30. The system of claim 28, comprising a means for computing a sleep state indication using cardio-respiratory variability and heart rate variability.

31. A machine-readable medium that provides instructions, which when carried out by one or more devices, cause the one or more devices to perform operations comprising:
receiving from an implantable device a signal associated with one or more heart contractions over a time period;
receiving a signal associated with a respiration over the time period;
determining a cardio-respiratory ratio of heart contractions to respiration cycles over the time period;
determining a cardio-respiratory variability of the cardio-respiratory ratio; and
computing a sleep state indication using the variability, wherein computing a sleep state indication using the variability includes comparing the variability to a threshold value.

32. The machine-readable medium of claim 31, comprising instructions for computing a sleep state indication using the variability and at least one other physiological indicator.

* * * * *